(12) United States Patent
Crockatt et al.

(10) Patent No.: US 11,603,361 B2
(45) Date of Patent: Mar. 14, 2023

(54) PROCESS AND SALTS FOR THE PREPARATION OF 2,5-FURANDICARBOXYLIC ACID

(71) Applicant: Nederlandse Organisatie voor toegepast-natuurwetenschappelijk onderzoek TNO, The Hague (NL)

(72) Inventors: Marc Crockatt, 's-Hertogenbosch (NL); Carol Andrea Roa Engel, Delfgauw (NL); Cornelis Petrus Marcus Roelands, Voorschoten (NL); Johannes Van Der Meer, Loenen aan de Vecht (NL)

(73) Assignee: Nederlandse Organisatie voor toegepastnatuurwetens, The Hague (NL)

( * ) Notice: Subject to any disclaimer, the term of this patent is extended or adjusted under 35 U.S.C. 154(b) by 0 days.

(21) Appl. No.: 17/274,296

(22) PCT Filed: Sep. 30, 2019

(86) PCT No.: PCT/NL2019/050654
§ 371 (c)(1),
(2) Date: Mar. 8, 2021

(87) PCT Pub. No.: WO2020/067901
PCT Pub. Date: Apr. 2, 2020

(65) Prior Publication Data
US 2021/0332021 A1    Oct. 28, 2021

(30) Foreign Application Priority Data
Sep. 28, 2018 (EP) .................... 18197773

(51) Int. Cl.
*C07D 307/68* (2006.01)

(52) U.S. Cl.
CPC .................. *C07D 307/68* (2013.01)

(58) Field of Classification Search
CPC ................................... C07D 307/68
(Continued)

(56) References Cited

U.S. PATENT DOCUMENTS 8,912,349 B2    12/2014    Shaikh et al.
2013/0345452 A1    12/2013    Janka et al.
(Continued)

FOREIGN PATENT DOCUMENTS

CA    2902493 A1    10/2014
WO    2012017052 A1    2/2012
(Continued)

OTHER PUBLICATIONS

Wikipedia I (Base (chemistry), Sep. 2017, p. 1-9) (Year: 2017).*
(Continued)

*Primary Examiner* — Taylor V Oh
(74) *Attorney, Agent, or Firm* — Hoffmann & Baron, LLP

(57) ABSTRACT

The invention is directed to a method for the preparation, in particular for the purification of 2,5-furandicarboxylic acid or a salt thereof, comprising crystallization of a 2,5-furandicarboxylic acid mono salt and then crystallizing 2,5-furandicarboxylic diacid from this mono salt. Preferably, the method is at least partially carried out in a continuous or semi-continuous manner, preferably at least partially in one or more continuous mixed-suspension mixed product removal (MSMPR) crystallizers in series.

20 Claims, 14 Drawing Sheets

(58) Field of Classification Search
USPC .......................................................... 549/485
See application file for complete search history.

(56) References Cited

U.S. PATENT DOCUMENTS

| | | | |
|---|---|---|---|
| 2018/0044312 A1* | 2/2018 | Van Krieken | ........ C07D 307/68 |
| 2020/0055832 A1 | 2/2020 | Crockatt et al. | |

FOREIGN PATENT DOCUMENTS

| | | |
|---|---|---|
| WO | 2014014979 A1 | 1/2014 |
| WO | 2014014981 A1 | 1/2014 |
| WO | 2014015256 A2 | 1/2014 |
| WO | 2014158838 A1 | 10/2014 |
| WO | 2014209112 A1 | 12/2014 |
| WO | 2016076712 A1 | 5/2016 |
| WO | 2016146753 A1 | 9/2016 |
| WO | 2016186504 A1 | 11/2016 |
| WO | 2016188605 A1 | 12/2016 |

OTHER PUBLICATIONS

Wikipedia II, Water of Crystallization, Feb. 2017, p. 1-8 (Year: 2017).*

Qin, Ye-Zhi, et al. "Enzyme-Catalyzed Selective Oxidation of 5-Hydroxymethylfurfural (HMF) and Separation of HMF and 2, 5-Diformylfuran Using Deep Eutectic Solvents," Green Chemistry, vol. 17, No. 7, pp. 3718-3722 (2015).

Triebl, Christoph, et al., "Simulation and Economic Analysis of 5-Hydroxymethylfurfural Conversion to 2, 5-Furandicarboxylic Acid," Computers & Chemical Engineering, vol. 52, pp. 26-34 (2013).

Hua, Carol, et al., "Systematic Tuning of Zn (II) Frameworks with Furan, Thiophene, and Selenophene Dipyridyl and Dicarboxylate Ligands," Crystal Growth & Design, vol. 17, No. 12 6262-6272 (2017).

Jaulmes, S., et al., "Furanne-2, 5-Dicarboxylate Acide de Potassium," Acta Crystallographica Section B: Structural Crystallography and Crystal Chemistry, vol. 38, No. 1, pp. 279-281 (1982).

Wiedmann, Timothy Scott, et al., "Pharmaceutical Salts: Theory, Use in Solid Dosage Forms and in Situ Preparation in an Aerosol," Asian Journal of Pharmaceutical Sciences, vol. 11, No. 6, pp. 722-734 (2016).

Li, Jicong, et al., "Multistage Continuous Mixed-Suspension, Mixed-Product Removal (MSMPR) Crystallization with Solids Recycle," Organic Process Research & Development, vol. 20, No. 2, pp. 510-516 (2016).

Erdemir, Deniz, et al., "Nucleation of Crystals from Solution: Classical and Two-Step Models," Accounts of Chemical Research, vol. 42, No. 5, pp. 621-629 (2009).

* cited by examiner

Powder diffractogram of 2H-FDCA crystals obtained at pH = 1 and at T = 20 °C

Microscopic image of small 2H-FDCA crystals obtained at pH = 1 and at T - 20 °C.

Powder diffractogram of 2H-FDCA crystals obtained at pH = 1 and at T = 80 °C

Microscopic image of large 2H-FDCA crystals obtained at pH=1 and at T=80 °C

Samples of 2H-FDCA crystals obtained at pH=1 and at T=20 °C (left) and at pH-1 and at T=80 °C (right)

Powder diffractogram of NaHDCA.1H2O crystals obtained in first step at pH =3 and at T = 0 °C Powder diffractogram of 2H-FDCA crystals obtained in second step at pH = 1 and at T = 20 °C Microscopic image of large NaHDCA.1H2O crystals obtained in vessel 1 at pH=3 and at T=20 °C Powder diffractogram of NaHDCA.1H2O crystals obtained in vessel 1 at ph = 3 and at T = 20 °C Powder diffractogram of 2H-FDCA crystals obtained n vessel 2 at pH = 1 and at T = 20 °C Thermogravimetric analysis (TGA) ON NaHFDCA.1H2O crystals with decrease in weight of approximately 10% at T = 138 °C corresponding to loss of crystal water

PROCESS AND SALTS FOR THE PREPARATION OF 2,5-FURANDICARBOXYLIC ACID

This application is the U.S. National Phase of International Patent Application Number PCT/NL2019/050654 filed Sep. 30, 2019, which claims priority to EP 18197773.7 filed Sep. 28, 2018 each of which is incorporated herein by reference.

The invention is in the field of the preparation of 2,5-furandicarboxylic acid. In particular, the present invention is directed to the purification of 2,5-furandicarboxylic acid or a salt thereof.

The compound 2,5-furandicarboxylic acid (2H-FDCA) is a promising starting point for the production of materials. For instance, 2H-FDCA has been suggested as a bio-based replacement of terephthalate for the production of plastic materials. Besides being bio-based, polyethylene furanoate (PEF) offers many advantages over polyethylene terephthalate (PET) with regards barrier and mechanical properties.

A particular route for the preparation of FDCA comprises oxidation of 5-(hydroxymethyl)furfural (HMF) by for instance biotechnological processes, electrochemical processes or chemically by air (see e.g. Triebl et al. *Computers and Chemical Engineering* 52 (2013) 26-34 and references cited therein). These processes generally result in a solution of 2H-FDCA or salt thereof from which 2H-FDCA must be isolated. A particular challenge herein is the provision of essentially colorless 2H-FDCA and low levels of impurities such as 5-formyl-2-furancarboxylic acid (FFCA).

Inter alia due to the instability of HMF, decomposition occurs which generally result in colored impurities, isolated 2H-FDCA may for instance be orange or brownish of color even if the amount of impurities is relatively low. Colored 2H-FDCA can result in colored plastic materials, which is not desirable. In addition, the intensity of the color can be taken as an indication of the amount of impurities, which may consequently interfere in the subsequent processing (e.g. polymerization) of the 2H-FDCA. For instance, FFCA is a mono-acid that can be present as an impurity and lead to chain termination in the polymerization process. As such, an effective and efficient method for purifying 2H-FDCA is desired to obtain a pure and an essentially colorless 2H-FDCA product.

WO 2016/146753 and WO 2014/209112 disclose purification of 2H-FDCA by a crystallization of 2H-FDCA from a solution of disodium furan-2,5-dicarboxylate by reducing the pH of said solution.

The present inventors surprisingly found that purification of 2H-FDCA can be improved using a 2,5-furandicarboxylic acid mono salt (FDCA mono salt). It was found that using the FDCA mono salt can result is a less colored 2H-FDCA and lower levels of impurities such as FFCA. In addition, the use of the FDCA mono salt enables a facile preparation method with particularly favorable down-stream processing (DSP) requirements, thereby enabling an improved efficiency of the overall 2H-FDCA production process.

The present inventors found that the FDCA mono salt can be crystallized as a monohydrate and, without wishing to be bound by theory, believe that this monohydrate results in a particularly pure salt form which can be used to increase the purity and colorlessness of the final 2H-FDCA product.

Accordingly, the present invention is directed to a method for the preparation, in particular for the purification, of 2,5-furandicarboxylic acid or a salt thereof, comprising crystallization of a 2,5-furandicarboxylic acid mono salt. The present invention is particularly directed to a method for the purification of impure 2,5-furandicarboxylic acid or a salt thereof, comprising providing impure 2,5-furandicarboxylic acid or a salt thereof, followed by crystallization of a 2,5-furandicarboxylic acid mono salt. The 2,5-furandicarboxylic acid mono salt can then, directly or indirectly, be converted into 2,5-furandicarboxylic acid or a salt thereof. More in particular, the present invention pertains to purification of impure 2,5-furandicarboxylic acid or a salt thereof comprising a two-step process comprising a first crystallization of the 2,5-furandicarboxylic acid mono salt, followed by a second step comprising crystallization of 2,5-furandicarboxylic acid.

Figure 1:
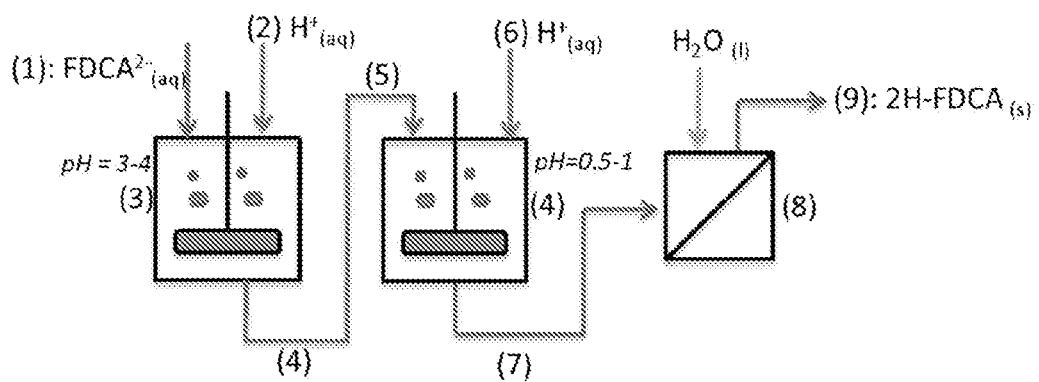
FIG. 1 schematically illustrates a particular embodiment of the invention.

With direct or indirect conversion of the 2,5-furandicarboxylic acid mono salt into 2,5-furandicarboxylic acid or a salt thereof is meant that this can be carried out in one or more steps and that other intermediate steps may also be part of the method to prepare the 2,5-furandicarboxylic acid or a salt thereof. The salt of 2,5-furandicarboxylic acid to which the 2,5-furandicarboxylic acid mono salt is converted may be any salt other than the mono salt that is crystallized and the preceding step.

With impure 2,5-furandicarboxylic acid or a salt thereof is meant herein a mixture comprising 2,5-furandicarboxylic acid or a salt thereof and impurities, the impurities being other compounds than 2,5-furandicarboxylic acid or the salt thereof. Typically, at least part of the impurities are colored, giving the impure 2,5-furandicarboxylic acid or a salt thereof its unfavorable color. The impure 2,5-furandicarboxylic acid or a salt thereof can be provided according to the invention in any state or form, e.g. as a solid, in solution, as a partial suspension, as well as combinations thereof. In a particular embodiment, it is provided in water.

The two carboxylate moieties in the compound 2,5-furandicarboxylic acid are each capable of forming ionic bonds with cations. As such, with the term '2,5-furandicarboxylic acid mono salt' or 'FDCA mono salt' is meant herein that one of these carboxylate moieties has an ionic interaction with a cation other than a proton, while the other carboxylate moiety has an interaction with a proton and is thus neutralized to the carboxylic acid. Accordingly, without the addition 'salt' or 'mono salt', the term '2,5-furandicarboxylic acid' herein means the fully neutralized or diacid form. For sake of clarity the fully neutralized or diacid form of 2,5-furandicarboxylic acid is herein abbreviated as 2H-FDCA. FDCA mono salt and 2H-FDCA can be illustrated with the following structures.

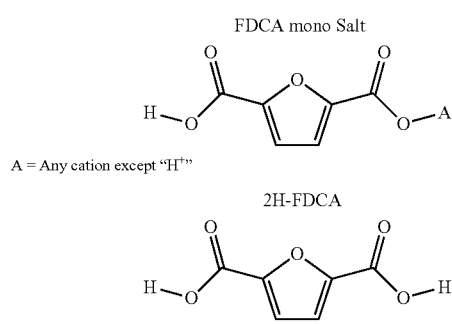

Preferably, the 2,5-furandicarboxylic acid mono salt comprises a cation selected from the group consisting of alkali metals, alkaline earth metals, ammonium cations, and combinations thereof, preferably sodium, potassium, magnesium, calcium, lithium, ammonium, tetraalkyl ammonium such a tetramethyl ammonium, and combinations thereof, more preferably sodium. As such, the 2,5-furandicarboxylic acid mono salt particularly preferably comprises the mono sodium salt of 2,5-furandicarboxylic acid. It may be appreciated that in the embodiments wherein the cation comprises a multivalent cation such as an alkaline earth metal, one of these cations is shared between two molecules of 2,5-furandicarboxylate.

In accordance with the present invention, the FDCA mono salt can be crystallized from a first aqueous fluid, typically an aqueous solution. This can be carried out by a step comprising providing the first aqueous fluid, e.g. an aqueous alkaline solution, comprising 2,5-furandicarboxylate, i.e. an dianionic form or dicarboxylate ion of 2H-FDCA, and decreasing the pH of this alkaline solution to about the highest $pK_a$-value of 2H-FDCA. The first aqueous liquid may also comprise at least part of the impurities present in the impure 2H-FDCA or salt thereof. The present inventors found that the $pK_a$-values of 2H-FDCA can advantageously be used to provide FDCA mono salt because, in aqueous solutions, the solubility of 2H-FDCA is lower than the anionic forms thereof. As such, decreasing the pH of a solution comprising 2,5-furandicarboxylate results in at least partial neutralization of the carboxylate moieties, a decreased solubility of the FDCA form and concomitant crystallization of the particular FDCA form. The specific form (i.e. charge and salt form) of the FDCA depend i.a. on the pH and polarity of the solution wherein the form is dissolved.

Accordingly, the present invention typically comprises providing a first aqueous fluid, typically a solution, comprising the FDCA mono salt and crystallizing the FDCA mono salt from said first aqueous fluid to provide a crystallized FDCA mono salt. The crystallization can be carried out by decreasing the pH of the first aqueous fluid comprising 2,5-furandicarboxylate. Preferably the pH of the first aqueous fluid is adjusted to 1.8 or higher, more preferably to a pH in the range of 2 to 6, more preferably to a pH of about 3. It was found that such pH can result in crystallization of the FDCA mono salt, or a hydrate such as the monohydrate thereof. It may be appreciated that the mono-salt might also (temporary) contain H2-FDCA (due to localized low pH at the addition point of the acid).

The crystallization of the FDCA mono salt is typically carried out at moderate temperatures, e.g. less than 50° C., preferably less than 30° C., more preferably less than 20° C. At these temperatures, in particularly at the above-mentioned pH ranges, large crystals of FDCA mono salt can be formed (e.g. an average mesh size of >100 μm). These large crystals facilitate filtration and washing (which are optional) and have a relatively lower surface area with respect to smaller crystals to which impurity can adhere.

In preferred embodiments, decreasing the pH of the first aqueous fluid is carried out by contacting the fluid with a strong acid. Typically, the use of concentrated strong acids is preferred as this limits the require for addition of large volumes of additional water, preventing dilution of the 2,5-furandicarboxylate or FDCA mono salt the amount of addition water and dilution of the 2,5-furandicarboxylate or FDCA mono salt. Adding more water is undesirable as this may increase dissolution and reduce isolated yield? Moreover, adding more water may require larger infrastructure and more associated costs. Particularly suitable strong acids include mineral acids such as sulfuric acid and/or hydrochloric acid.

Adjusting the pH of a solution to induce crystallization of a compound is known in the art as pH-shift crystallization. Although such a method is preferred for the present invention, additional or alternative crystallization methods may also advantageously be used for the present invention. For instance, crystallization of the 2,5-furandicarboxylic acid mono salt can further be assisted by standard techniques such as decreasing the temperature, seeding, addition of anti-solvents and the like.

The crystallization of the FDCA mono salt from the first aqueous fluid generally results in a fluid, such as a suspension, comprising the crystallized FDCA mono salt (herein also referred to as the FDCA mono salt product fluid). Further processing of the crystallized FDCA mono salt generally comprises providing a second aqueous fluid comprising the crystallized FDCA mono salt and subsequent crystallization of the neutralized FDCA from this second aqueous fluid.

To provide said second aqueous fluid, the crystallized FDCA mono salt can be maintained in the FDCA mono salt product fluid, or the crystallized FDCA mono salt can be isolated from the FDCA mono salt product fluid by filtration to form a residue comprising the FDCA mono salt, or a combination thereof (i.e. a part of the FDCA mono salt is maintained in the FDCA mono salt product fluid and a part is isolated). In the embodiment wherein the crystallized FDCA mono salt in the aforementioned suspension is maintained in the fluid, said product fluid can be considered as the second aqueous fluid.

The filtration of the FDCA mono salt product fluid generally includes washing of the residue in order to remove possible impurities. After the optional washing, the residue comprising the FDCA mono salt is typically a solid residue which may contain some remaining amounts of solvents from the washing procedure. The solid residue is thus not necessarily dry.

In the embodiments that comprise filtration of the FDCA mono salt to form a solid residue comprising the FDCA mono salt, the second aqueous fluid is typically obtained by contacting (e.g. mixing, blending and/or combining) the residue comprising the FDCA mono salt with a fresh aqueous fluid, typically an aqueous solution or water. Filtration of the FDCA mono salt product fluid and contacting the obtained residue with said fresh aqueous fluid may particularly be advantageous since the crystallization of 2H-FDCA from a relatively clean fluid of the FDCA mono salt can provide higher purities of the crystallized 2H-FDCA. In addition, the intermediate filtration of the FDCA mono salt enables the possibility to carry out the subsequent steps (including crystallization of 2H-FDCA) at higher temperatures (e.g. 80° C. or more). Crystallization of 2H-FDCA at these higher temperatures can result in larger crystals of 2H-FDCA, which facilitates filtration and washing thereof. On the other hand, the embodiments that comprise maintaining the crystallized FDCA mono salt in the product fluid (i.e. without the intermediate filtration) can be advantageous for reasons of a higher possible final yield of the crystallized 2H-FDCA. In contrast to the embodiments comprising filtration, no FDCA mono salt is lost due to washing of the residue and/or disposal of the mother liquid or filtrate. It may therefore be preferred to use a combination of both embodiments.

The crystallized 2H-FDCA can be filtered and washed to obtain a residue comprising 2H-FDCA. This residue is typically solid, and preferably, but not necessarily, dry. Besides 2H-FDCA, the residue may also comprise minor amounts (e.g. trace amounts) FDCA mono salt, in particular if it is obtained from a continuous mixed-suspension mixed product removal crystallizer as described herein below. However, such minor amounts are not typical since the FDCA mono salt dissolves readily at low pH such as about pH 1.

The crystallization of 2H-FDCA from the second aqueous fluid can be carried out similarly as the crystallization of the FDCA mono salt, with typical differences being a different pH, temperature and concentration of the FDCA form in solution (due to solubility differences). Generally, 2H-FDCA is crystallized from the second aqueous fluid by adjusting the pH to below 1.8, preferably to a pH in the range of 0 to 1.7, more preferably in the range of 0.5 to 1.5 such as about 1.

The crystallization of the 2H-FDCA is typically carried out at higher temperatures, e.g. more than 50° C., preferably more than 80° C., and more preferably between 80° C. and 130° C. At these temperatures, in particular at the above-mentioned pH ranges, large crystals of 2H-FDCA can be formed (e.g. an average mesh size of >100 μm). These large crystals facilitate filtration and washing and have a relatively lower surface area with respect to smaller crystals to which impurity can adhere.

The second aqueous fluid may be a suspension or a solution comprising the FDCA mono salt. The solution comprising the FDCA mono salt is herein referred to as the intermediate solution.

The intermediate solution can be obtained by heating after or during contacting (e.g. mixing, blending and/or combining) the residue comprising the FDCA mono salt with the fresh aqueous fluid as described herein-above. Dissolving the crystallized 2,5-furandicarboxylic acid mono salt can be carried out at moderate or elevated temperatures. For the present invention moderate temperatures are preferred to limit degradation and/or polymerization of side-products resulting in coloration of the final 2H-FDCA product. Moderate temperatures herein typically mean temperatures in the range of 0 to 90° C., while elevated temperatures herein typically mean temperatures of 90° C. or higher.

Typically, the intermediate solution has a pH similar to that of the pH to which the first aqueous fluid is adjusted in induce crystallization of the FDCA mono salt. However, the pH may also be different and may for instance be higher to promote dissolution of the FDCA mono salt. In a preferred embodiment, the present method comprises reducing the pH of the intermediate solution is such that the second aqueous solution, i.e. the solution from which 2H-FDCA is crystallized, is obtained.

In the embodiment wherein the pH of the first and second aqueous fluids are decreased, the method of the present invention can be regarded as a two-step pH-shift crystallization method. An advantage of the two-step pH-shift crystallization method in accordance with the present invention over a one-step pH-shift crystallization is that a higher purity of 2H-FDCA can be achieved. By using the present two-step pH-shift crystallization method, crystals of 2H-FDCA can grow into crystals with less imperfections and inclusions of impurities compared to a conventional one-step pH-shift crystallization process.

The present inventors further surprisingly found that the present method is preferably at least partially carried out in a continuous or semi-continuous manner, for example at least partially in one or more continuous mixed-suspension mixed product removal (MSMPR) crystallizers in series. It was surprisingly found that the crystallization of 2H-FDCA from the second aqueous fluid in a continuous MSMPR crystallizer results in the formation of relatively large, e.g. an average mesh size of >100 μm, monodisperse crystals comprising 2H-FDCA. In comparison, a single step pH-shift process carried out in batch resulted in relative fine precipitates of 2H-FDCA that have a lot of surface area (difficult to wash) and likely contain inclusions and built-in impurities such a 5-formyl-2-furancarboxylic acid (FFCA) that is known to terminate polymerization of 2H-FDCA.

More specifically, the present invention preferably comprises crystallization of the 2,5-furandicarboxylic acid mono salt from the first aqueous fluid carried out in one or more first continuous MSMPR and crystallization of 2,5-furandicarboxylic acid from the second aqueous solution fluid out in one or more second MSMPR crystallizer that is connected to the first MSMPR crystallizer. In particular on industrial scale, it might be advantageous to use more than two crystallizers in total—e.g. in a configuration when there is a maturing time at a specific pH in an intermediate MSMPR, or in a configuration where the pH is brought down through several MSMPR gradually (i.e. one MSMPR at pH 5, one at pH 4, one a pH 3, then isolation, then another MSMPR at pH 2 followed by one MSMPR at pH 1) to afford larger crystals.

Figure 2:
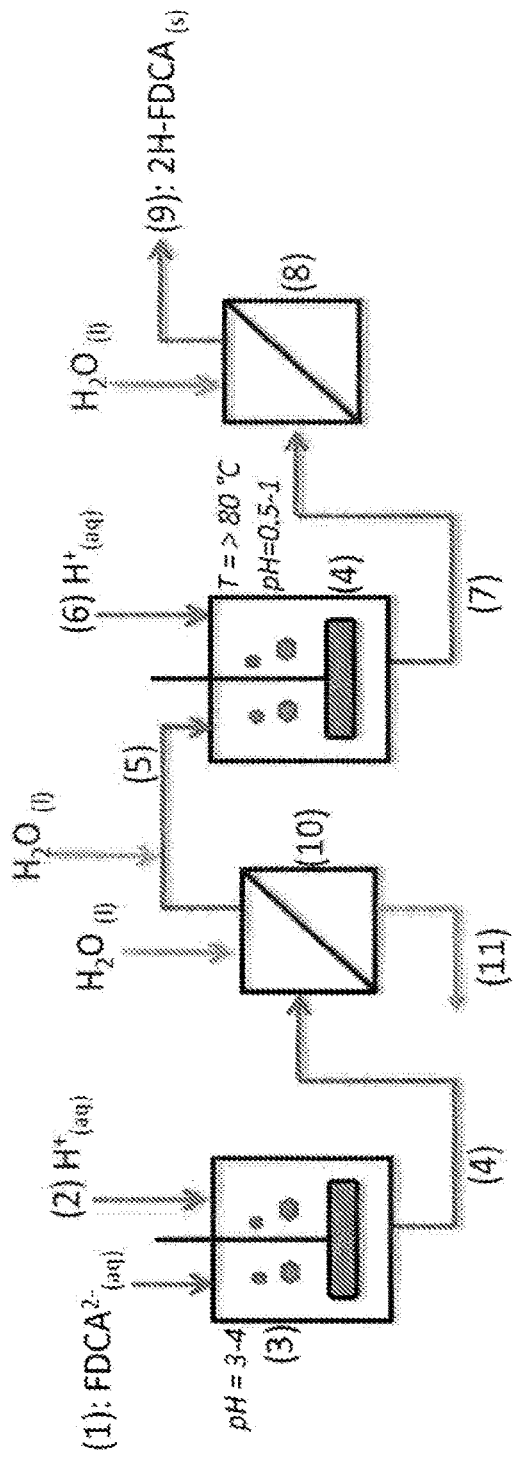
FIG. 2 schematically illustrates another particular embodiment of the invention.
Figure 3:
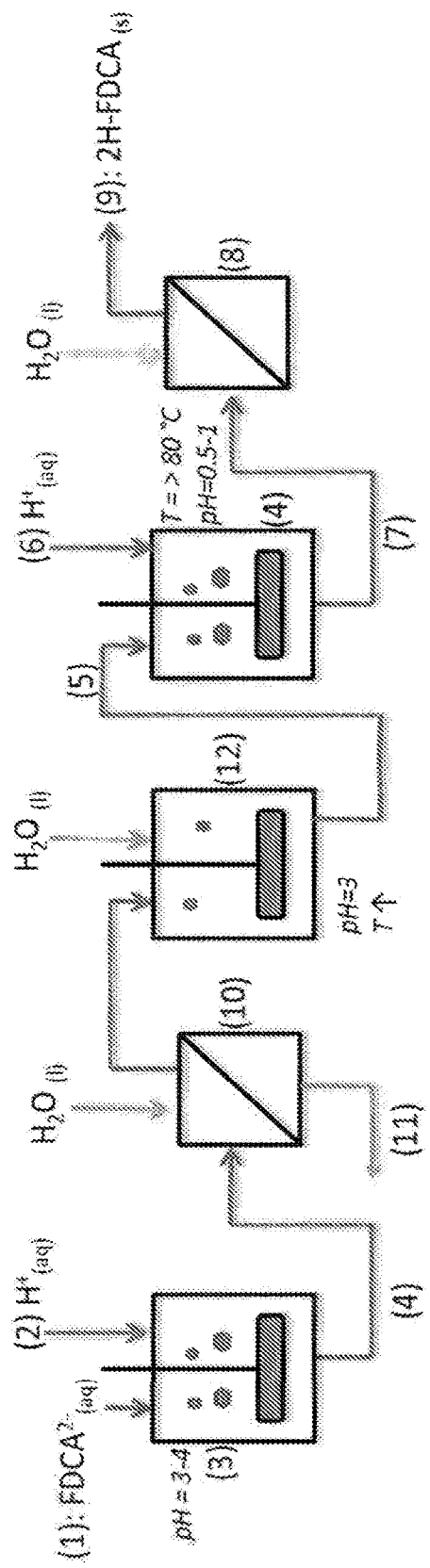
FIG. 3 schematically illustrates yet another particular embodiment of the invention.

To illustrate the present invention, three specific non-limiting embodiments in accordance with the present invention are provided and illustrated with FIGS. 1-3. In each of these embodiments, a stream of the first aqueous fluid (1) comprising the dicarboxylate of FDCA ($FDCA^{2-}_{(aq)}$ having a pH of more than 6 and a first stream of an acid (2, $H^{+}_{(aq)}$) such as concentrated sulfuric acid are added to the first continuous MSMPR (3). By addition of the first aqueous fluid (1) to the first continuous MSMPR (3), its pH is adjusted to around pH 3-4. This results in crystallization of the FDCA mono salt and the product fluid (i.e. a suspension) comprising the crystallized FDCA mono salt (4).

Subsequently, in a first particular embodiment which is illustrated in FIG. 1, the crystallized FDCA mono salt is maintained in the FDCA mono salt fluid (4) and directly added to a second MSMPR (4) as the second aqueous fluid (5), together with a second stream of an acid (6, $H^+_{(aq)}$) such as concentrated sulfuric acid. By addition of the second aqueous fluid (5) to the second continuous MSMPR (4), its pH is adjusted to around pH 0.5-1.5 at moderate temperature (preferably at less than 50° C., more preferably less than 20° C.). This results in formation of a stream comprising the crystallized 2H-FDCA (7). This crystallized 2H-FDCA is then isolated by filtration and washed in a filtration device (8) to yield a residue comprising high purity, relatively low-colored 2H-FDCA product (9).

Alternatively, in a second particular embodiment which is illustrated in FIG. 2, the crystallized FDCA mono salt is isolated by filtration from FDCA mono salt fluid (4), and washed in filtration device (10) to remove a significant amount of the impurities (11). The residue comprising the FDCA mono salt is then re-suspended in water to form the second aqueous fluid (i.e. a suspension, 5) which is led into the second continuous MSMPR (4), together with a second stream of acid (6). By addition of the second aqueous fluid (5) to the second continuous MSMPR (4), its pH is adjusted to around pH 0.5-1 at high temperature (preferably at least 80° C.). This results in formation of a stream comprising the crystallized 2H-FDCA (7). This crystallized 2H-FDCA is then isolated by filtration, and washed, in a filtration device (8) to yield the residue comprising high purity, relatively low-colored 2H-FDCA product (9).

In yet an alternative, third particular embodiment of the present invention, which is illustrated in FIG. 3, the crystallized FDCA mono salt is isolated by filtration and washed, in filtration device (10) to remove a significant amount of the impurities (11). The residue comprising the FDCA mono salt is then re-suspended in water and the suspension is heated in a dissolution vessel (12), generally to a temperature of more than 80° C. at a pH of about 3, to obtain the intermediate solution (5). The intermediate solution is led into the second continuous MSMPR (4), together with a second acid stream (6). By addition of the second aqueous fluid (5) to the second continuous MSMPR (4), its pH is adjusted to around pH 0.5-1 at high temperature (preferably at least 80° C.). This results in formation of a stream comprising the crystallized 2H-FDCA (7). This crystallized 2H-FDCA is then isolated by filtration, and washed, in a filtration device (8) to yield the residue comprising high purity, relatively low-colored 2H-FDCA product (9).

The present invention can be further illustrated by the following non-limiting experimental examples.

COMPARATIVE EXAMPLE 1—ONE-STEP BATCH CRYSTALLIZATION OF 2H-FDCA AT AMBIENT TEMPERATURE

To a solution of 2,5-furandicarboxylate having a pH of 10 at 20° C. was added sulfuric acid to adjust the pH to 1. Small crystals of 2H-FDCA were formed which contain impurities and difficult to wash, though whitish.

Figure 4:
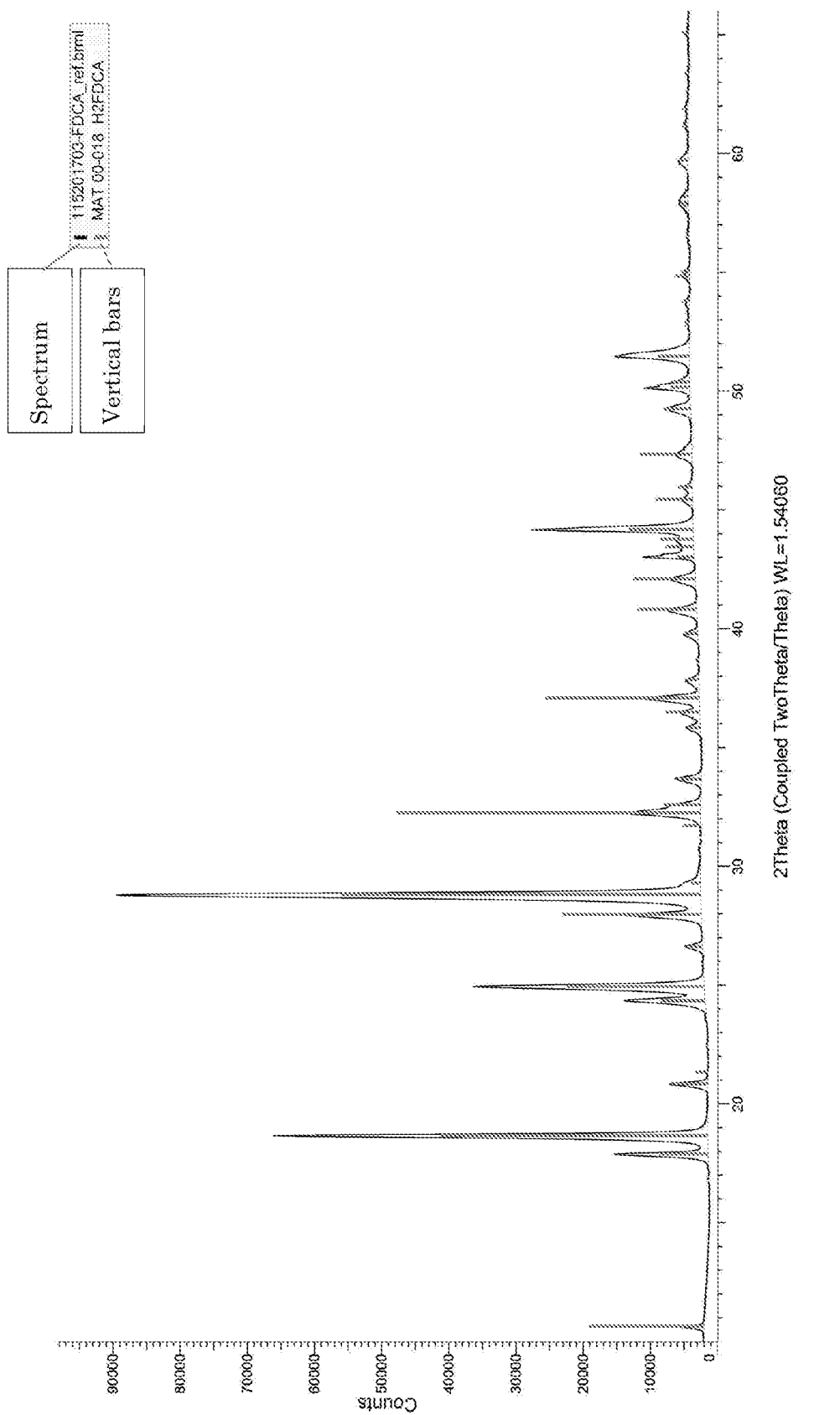
FIGS. 4 and 5 respectively show a powder X-ray diffraction (pXRD) pattern and a microscopic image of 2H-FDCA crystals obtained from a one-step batch crystallization process of 2H-FDCA at 20° C. as described in Comparative example 1.
Figure 5:
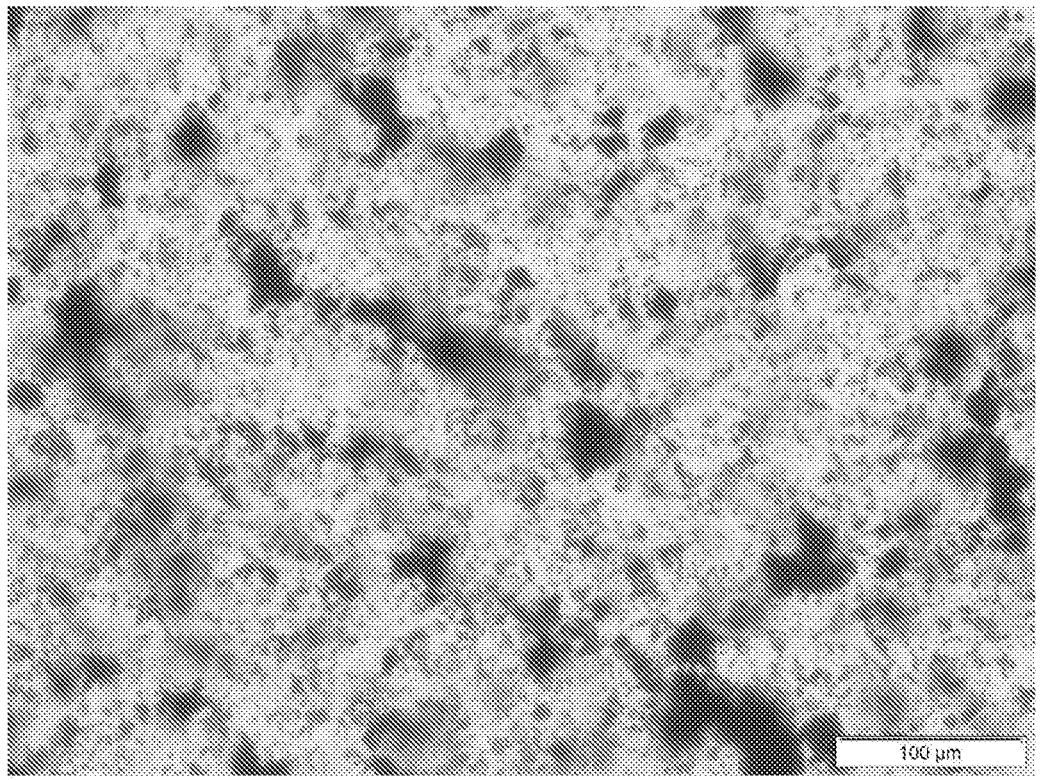

A powder diffractogram was recorded (FIG. 4) and microscopic images were taken (FIG. 5).

COMPARATIVE EXAMPLE 2—ONE-STEP BATCH CRYSTALLIZATION OF 2H-FDCA AT ELEVATED TEMPERATURE

To a solution of 2,5-furandicarboxylate having a pH of 10 at 80° C. was added sulfuric acid to adjust the pH to 1. Larger crystals of 2H-FDCA were formed than in comparative example 1, likely to contain less impurities and easy to wash, but colored yellowish.

Figure 6:
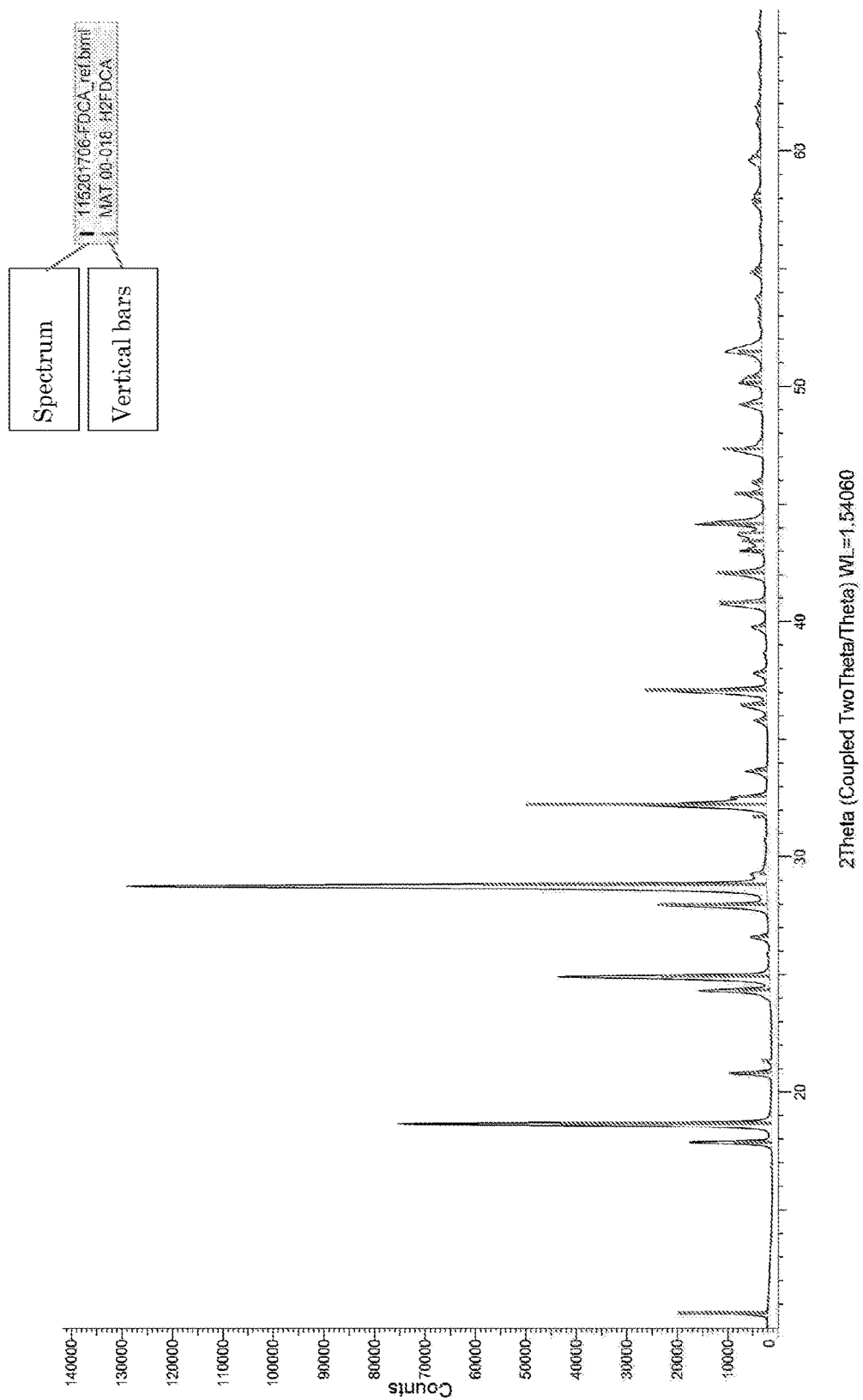
FIGS. 6 and 7 respectively show a pXRD pattern and a microscopic image of 2H-FDCA crystals obtained from a one-step batch crystallization process of 2H-FDCA at 80° C. as described in Comparative example 2.
Figure 7:
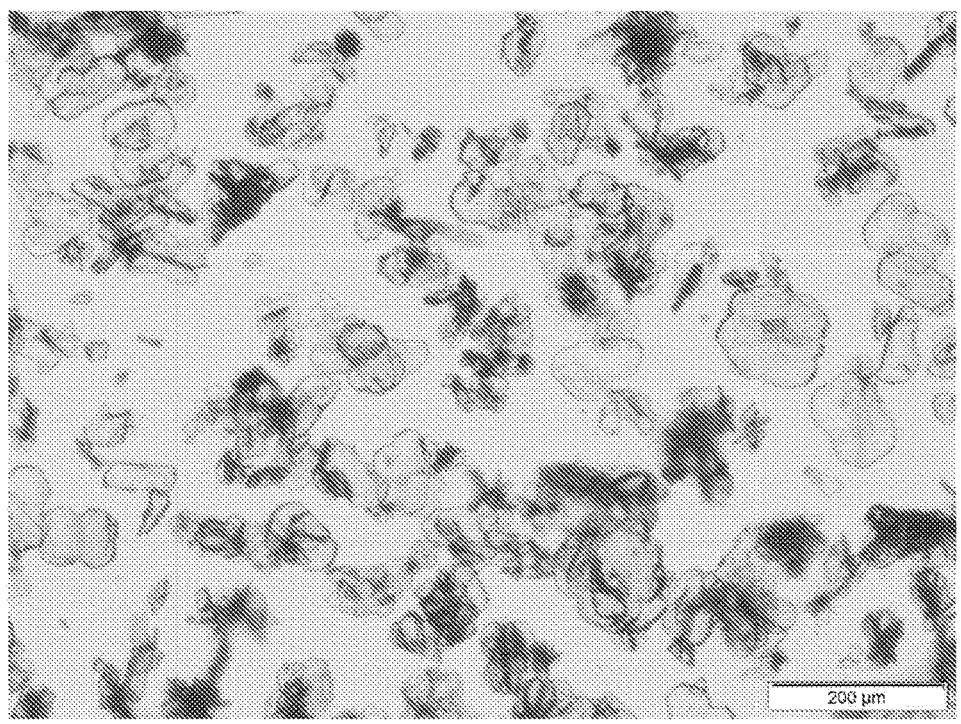

A powder diffractogram was recorded (FIG. 6) and microscopic images were taken (FIG. 7).

Figure 8:
FIG. 8 shows photographs of 2H-FDCA obtained from the one-step batch crystallization processes of 2H-FDCA at 20° C. (left) and 80° C. (right).

In FIG. 8, a photograph is illustrated showing samples of 2H-FDCA crystals obtained at pH=1 and at T=20° C. (left, comparative example 1) and at pH=1 and at T=80° C. (right, comparative example 2). Crystals obtained at T=80° C. are more discolored

EXAMPLE 1—TWO-STEP BATCH CRYSTALLIZATION OF 2H-FDCA

To a solution of 2,5-furandicarboxylate having a pH of 10 at 20° C. was added sulfuric acid at a range of 0.2 ml/min to adjust the pH to about 3. Formation of monoacid salts NaHFCDA, KHFDCA and NH$_4$HFDCA was observed. Samples of such crystals could be separated from the solution for analysis. Next, to the suspension more sulfuric acid was added at a range of 0.2 ml/min to adjust the pH to about 1. Recrystallization took place with monoacid salt crystals recrystallizing into 2H-FDCA crystals. Samples of such crystals could be separated from the solution for analysis.

Figure 10:
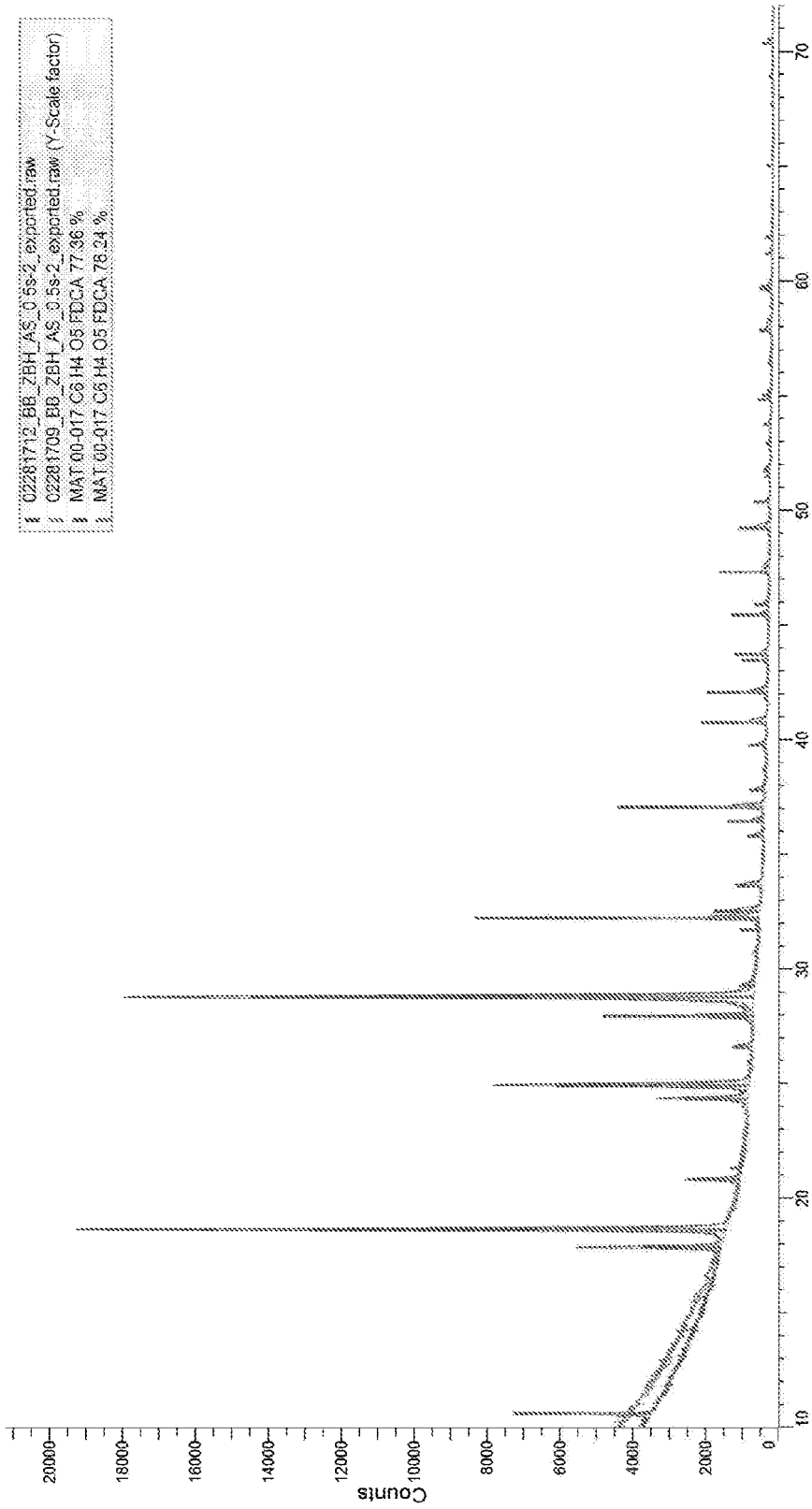

At ambient temperature (i.e. about 20° C.) small 2H-FDCA crystals were obtained by recrystallization that are difficult to wash and that contain impurities, although whitish appearance. With pXRD the diffraction pattern was measured (FIG. 10).

At elevated temperature (i.e. about 80° C.) larger 2H-FDCA crystals were obtained by recrystallization that are easier to wash but with yellowish appearance.

Figure 9:
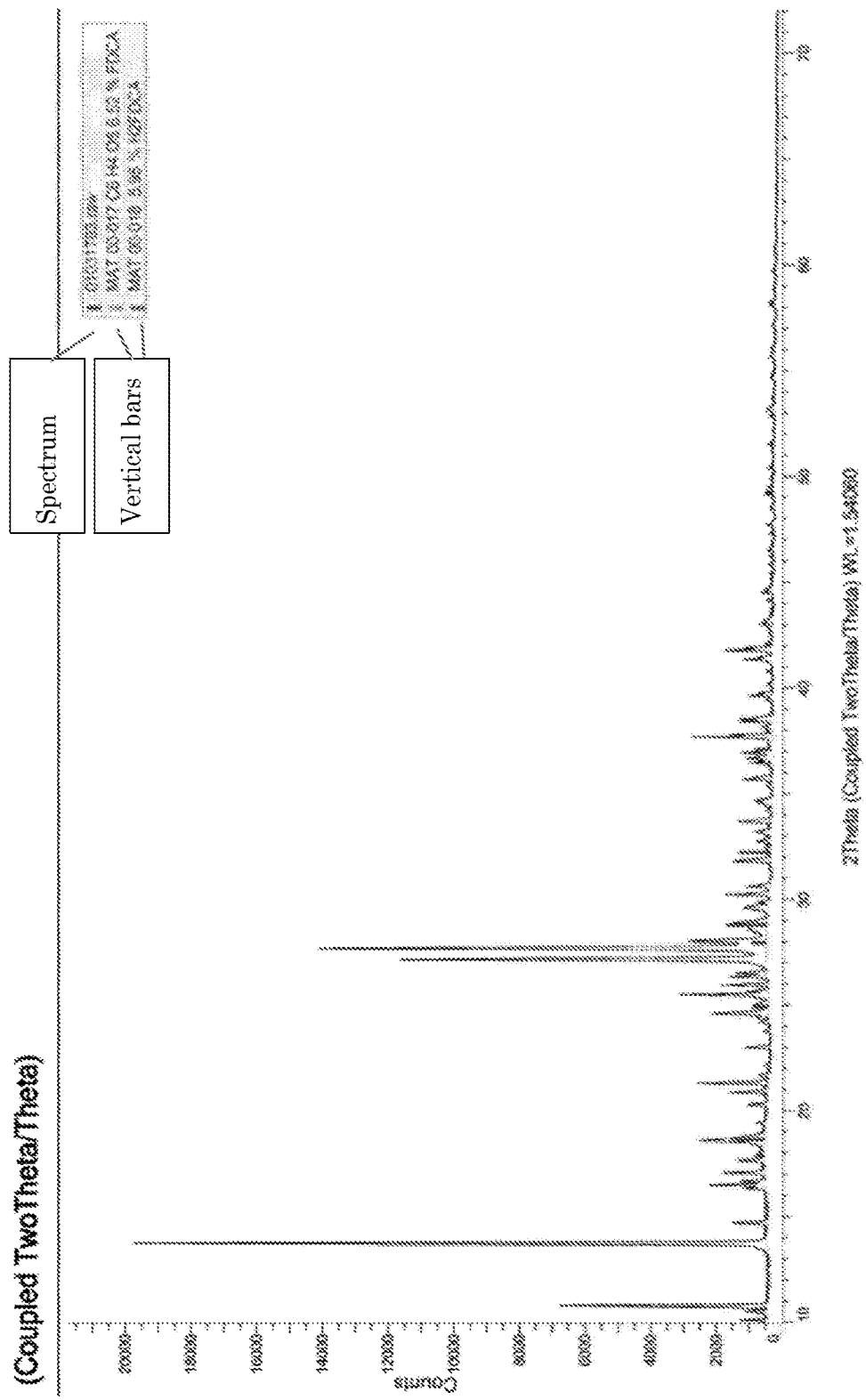
FIGS. 9 and 10 show pXRD patterns of respectively NaHFDCA.1H$_2$O and 2H-FDCA crystals obtained from crystallization of 2H-FDCA as described in Example 1.
Figure 14:
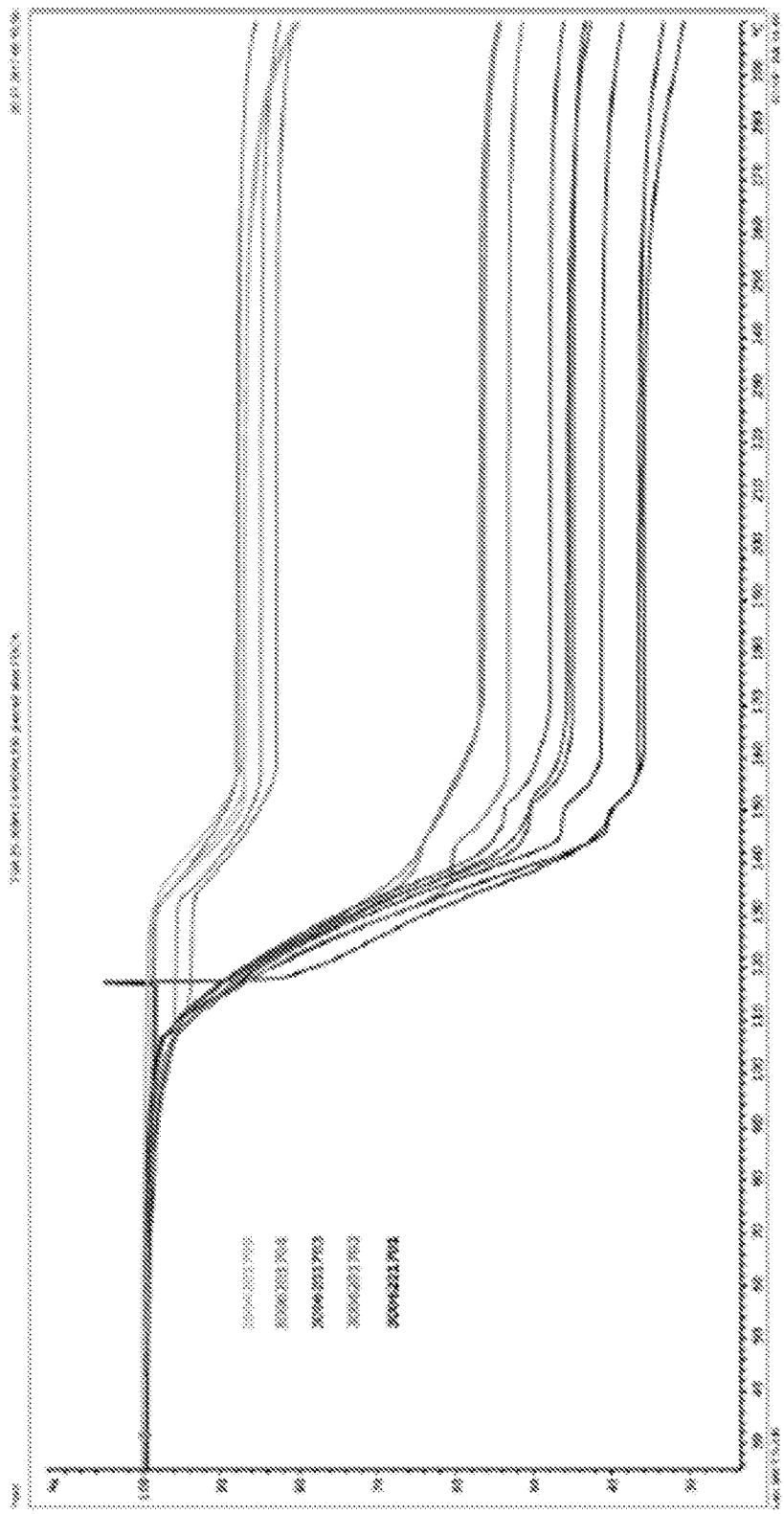
FIG. 14 shows the results of a thermogravimetric analysis on NaHFDCA.1H$_2$O crystals.

The NaHFDCA crystals were analyzed with (inductively coupled plasma-based analysis) ICP on Na$^+$ content, with HPLC on FDCA content (Table 1), and with pXRD the diffraction pattern was measured (FIG. 9). It was observed that the obtained crystals had a composition that corresponds with the mono-hydrate salt NaHFDCA.1H$_2$O (see also FIG. 14).

It is noted that the vertical bars as indicated in FIGS. 4, 6 9, 10, 12 and 13 are the position of the peaks in a reference spectrum of pure 2H-FDCA.

TABLE 1

Comparison of analysis results on samples of (a) NaHFDCA•1H$_2$O crystals obtained at pH = 3 and at T = 0° C. and (b) 2H-FDCA crystals obtained at pH = 1 and at T = 20° C.

| Samples | HPLC FDCA [mg/mg] | ICP Na$^+$ [mg/L] |
|---|---|---|
| pH = 3 T = 0° C. NaHFCDA•H$_2$O | 0.76 | 39 |
| pH = 1 T = 20° C. 2-HFDCA | 0.95 | 0.7 |

EXAMPLE 2—TWO-STEP CONTINUOUS CRYSTALLIZATION OF 2H-FDCA

Figure 11:
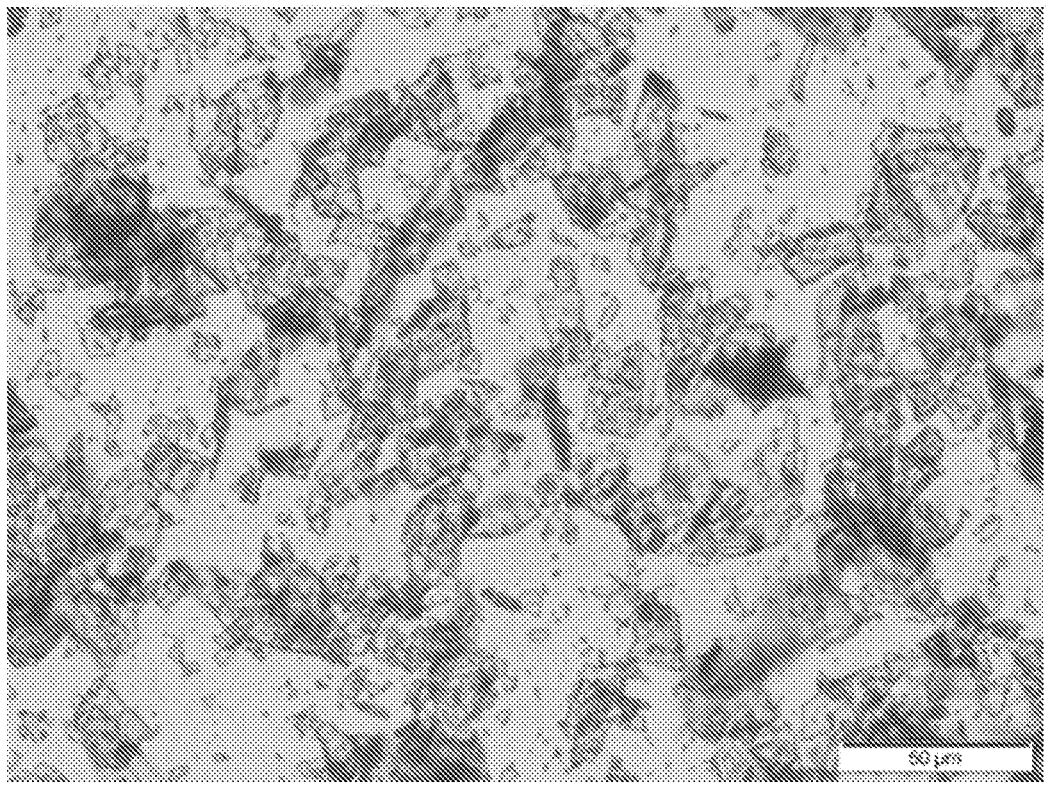
FIGS. 11 and 12 respectively show a microscopic image and a pXRD pattern of NaHFDCA.1H$_2$O crystals obtained as described in Example 2.
Figure 12:
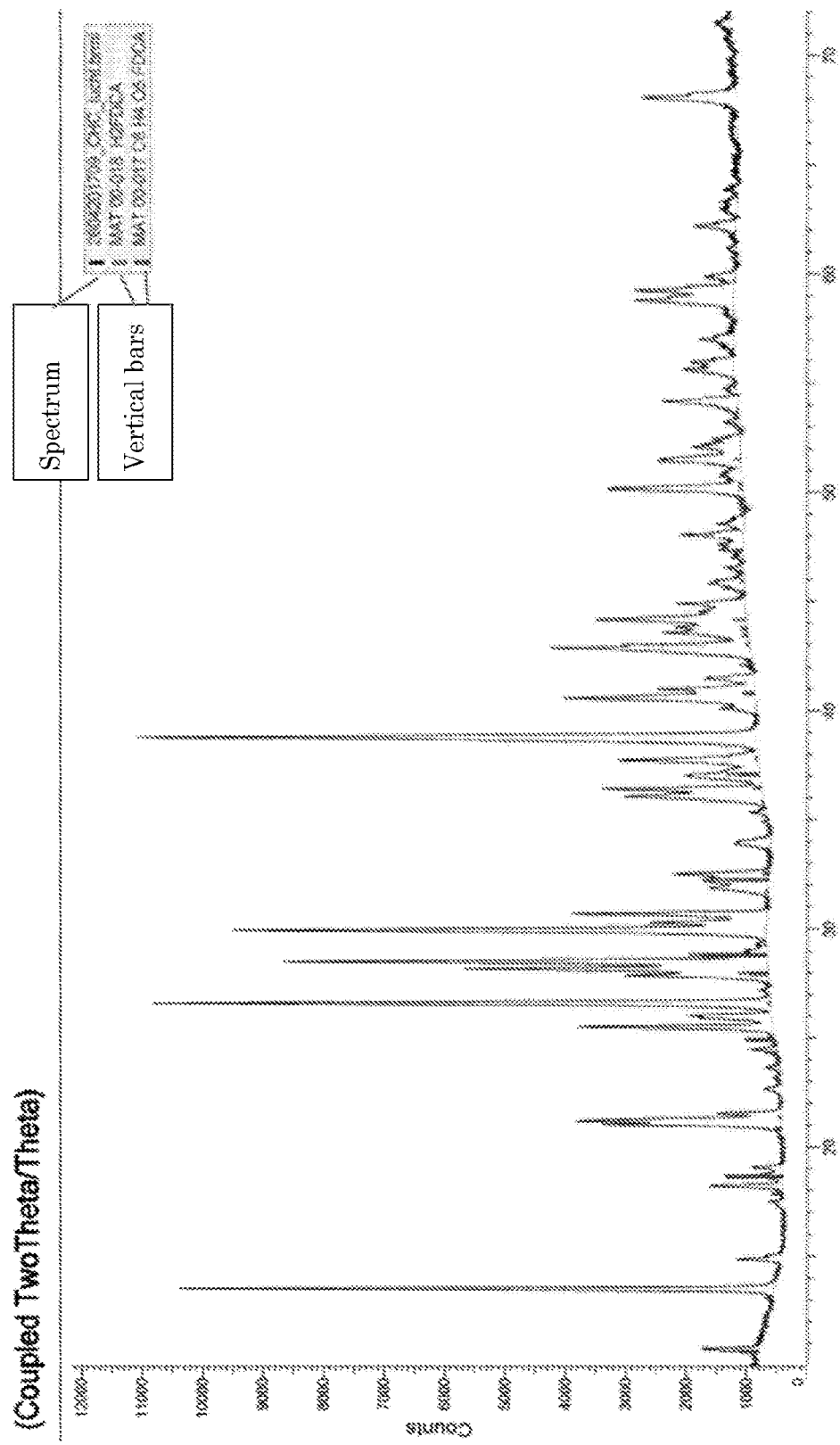

A stream of a solution of 2,5-furandicarboxylate having a pH of 10 and a stream of sulfuric acid were continuously fed and mixed in an MSMPR crystallizer in such a ratio that the pH was kept to 3 while a product stream containing monoacid salt crystals was continuously removed. Samples of such crystals could be separated from the solution for analysis. With pXRD the diffraction pattern was measured (FIG. 12) and microscopic images were taken (FIG. 11).

Figure 13:
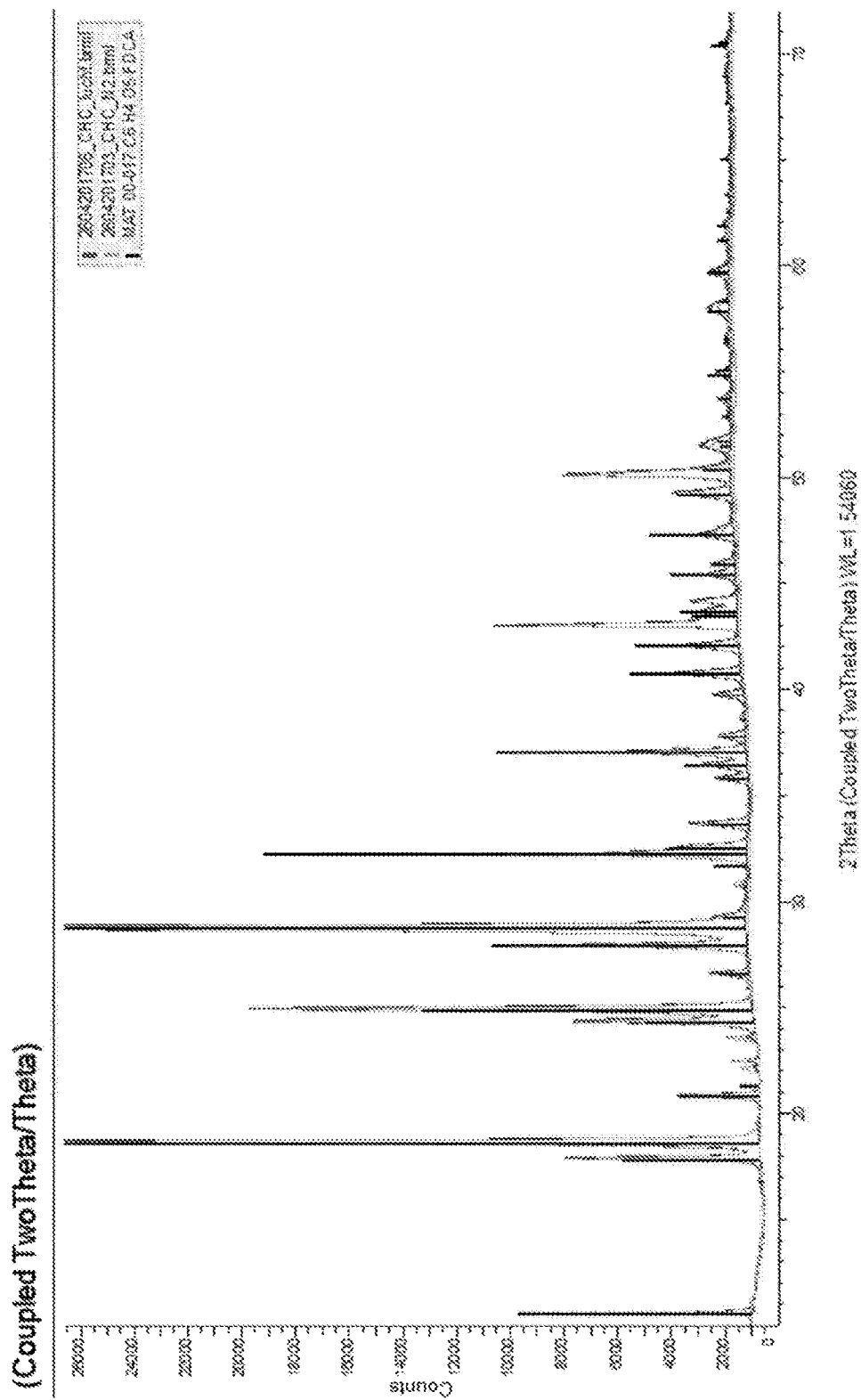
FIG. 13 shows a pXRD pattern of 2H-FDCA crystals obtained as described in Example 2.

Next, a stream of suspension of monoacid salt crystals having a pH of 3 and a second stream of sulfuric acid were continuously fed and mixed in an MSMPR crystallizer in such a ratio that the pH was kept to 1 while a product stream containing 2H-FDCA crystals was continuously removed. Recrystallization took place in the second MSMPR with monoacid salt crystals recrystallizing into 2H-FDCA crystals. Samples of such crystals could be separated from the solution for analysis. With pXRD the diffraction pattern was measured (FIG. 13).

With the first step at pH=3 in the first MSMPR at ambient temperature (i.e. about 20° C.), large NaHFDCA.1H2O crystals were obtained that are easy to wash and that contain little impurities and that have a whitish appearance. Transfer of these large NaHFDCA.1H2O crystals to the second step at pH=1 in the second MSMPR at elevated temperature (i.e. about 80° C.), resulted in recrystallization of the large NaHFDCA.1H2O crystals towards large 2H-FDCA crystals that are easy to wash and that contain little impurities, and also have a whitish appearance. These crystals meet the requirements for polymerization to PEF. The NaHFDCA crystals were analyzed with $H^+$ titration, (inductively coupled plasma-based analysis) ICP on $Na^+$ content, with HPLC on FDCA content (Table 2). It was observed that the obtained crystals had a composition that corresponds with the mono-hydrate salt NaHFDCA.1$H_2$O (see also FIG. 14).

TABLE 2

Comparison of analysis results on samples of (a) NaHDCA•1$H_2$O obtained in vessel 1 at pH = 3 and at T = 20° C. and (b) 2H-FDCA crystals obtained in vessel 2 at pH = 1 and at T = 20° C.

| Samples | Titration $H^+$ [mmol/g] | HPLC FDCA [mg/mg] | ICP $Na^+$ [mg/L] |
|---|---|---|---|
| Vessel 1 pH = 3 T = 20° C. NaHFCDA•$H_2$O | 5.9 | 0.68 | 46 |
| Vessel 2 pH = 1 T = 20° C. 2H-FDCA (1) | 14.7 | 0.95 | 7.2 |
| Vessel 2 pH = 1 T = 20° C. 2H-FDCA (2) | 14.5 | 0.91 | 9.4 |

EXAMPLE 3—TWO-STEP CRYSTALLIZATION OF 2H-FDCA VIA FDCA MONO SALT

A sample of 2H-FDCA (102.5 g—crude material from a biotech production batch) in water (1 L) was prepared of with the pH was adjusted to 9.81 with sodium hydroxide. The mixture was subsequently filtered three times through a 0.45 μm filter.

Figure 15:
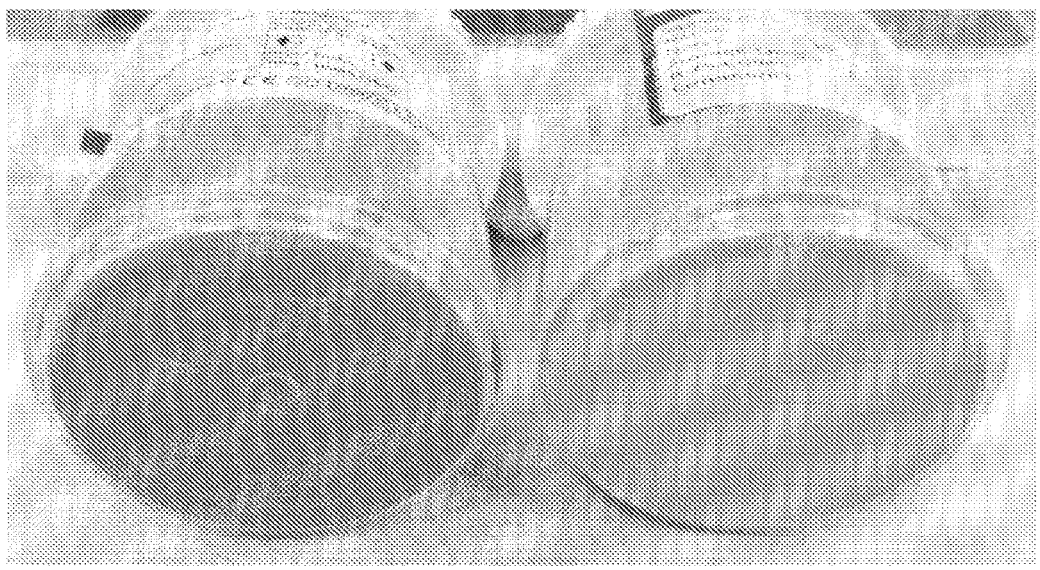
FIG. 15 shows a photograph of a solid obtained as described in Example 3.

An amount of 421.1 g of the mixture (~400 ml) was taken and adjusted to pH 3.01 with sulfuric acid, resulting in precipitation of a solid (i.e. FDCA mono salt). This was left to stir at room temperature for 3 hours, in which time the pH drifted to 2.53. The precipitated solid was isolated by filtration, and washed with water. The sample was then dried in a vacuum oven. The dried solid was then mixed with water and heated to 80° C. The pH was then adjusted to 0.85 with sulfuric acid, and then the mixture was then cooled to room temperature and the formed solid (i.e. 2H-FDCA) was isolated by filtration, and washed with water. The sample was then dried in a vacuum oven. The color of the formed solid was off-white to yellowish (see FIG. 15, right hand sample).

COMPARATIVE EXAMPLE 3—TWO-STEP CRYSTALLIZATION OF 2H-FDCA VIA 2NA-FDCA SALT

For this comparative example, 2H-FDCA was purified in a method with steps described in WO 2014/209112, in particular according to Example 1 described in WO 2014/209112.

As described in Example 3, a sample of 2H-FDCA (102.5 g—crude material from a biotech production batch) in water (1 L) was prepared of with the pH was adjusted to 9.81 with sodium hydroxide. The mixture was subsequently filtered three times through a 0.45 μm filter.

Next, an amount of 473.4 g of the mixture (~450 ml in volume) was adjusted the pH to ~7.0 with sulfuric acid and stirring, then this was cooled to −6.5° C. at which point the whole mixture solidified. The mixture was allowed to warm to −4.17° C. at which point a slurry was present. The slurry was allowed to stir for a time, after which the solids were removed by filtration (also at −4.17° C.). The filtrates were collected for further processing. The ice was melted to check that no FDCA related solids were present—none were found. The filtrates (235.5 g) were then adjusted to pH 1.14 (at room temperature) with sulfuric acid, resulting in precipitation of a solid. This slurry was left to stir for 1 hour, then the solid (i.e. 2H-FDCA) was isolated by filtration, and washed with water. The sample was then dried in a vacuum oven. The color of the formed solid was off-yellow to brownish (see FIG. 15, left hand sample). The formed solid clearly contained more contaminants than that of Example 3.

The invention claimed is:

1. A method for the purification of 2,5-furandicarboxylic acid or a salt thereof, comprising providing impure 2,5-furandicarboxylic acid or a salt thereof and crystallizing a 2,5-furandicarboxylic acid mono salt.

2. The method in accordance with claim 1, wherein the 2,5-furandicarboxylic acid mono salt comprises a cation selected from the group consisting of alkali metals, alkaline earth metals, ammonium cations, and combinations thereof.

3. The method in accordance with claim 1, comprising the steps of providing a first aqueous fluid comprising 2,5-furandicarboxylate and crystallizing the 2,5-furandicarboxylic acid mono salt from said first aqueous fluid to provide a crystallized 2,5-furandicarboxylic acid mono salt.

4. The method in accordance with claim 3, wherein crystallizing the 2,5-furandicarboxylic acid mono salt is carried out by adjusting the pH of the first aqueous fluid to a pH of 1.8 or higher.

5. The method in accordance with claim 3, wherein the method further comprises providing a second aqueous fluid, comprising the crystallized 2,5-furandicarboxylic acid mono salt and crystallizing 2,5-furandicarboxylic diacid from said second aqueous fluid to provide crystallized 2,5-furandicarboxylic acid.

6. The method in accordance with claim 5, wherein crystallizing the 2,5-furandicarboxylic diacid is carried out by adjusting the pH of the second aqueous fluid to a pH lower than 1.8.

7. The method in accordance with claim 5, wherein crystallizing the 2,5-furandicarboxylic acid mono salt results in a suspension comprising the crystallized 2,5-furandicarboxylic acid mono salt and wherein the method preferably further comprises filtration of the crystallized 2,5-furandicarboxylic acid mono salt to provide a residue comprising the 2,5-furandicarboxylic acid mono salt.

8. The method in accordance with claim 7, wherein said aqueous second fluid is obtained by contacting the residue comprising the 2,5-furandicarboxylic acid mono salt with an aqueous fluid, and then optionally heated to at least partially dissolve 2,5-furandicarboxylic acid mono salt.

9. The method in accordance with claim 5, wherein the method further comprises filtration of the crystallized 2,5-furandicarboxylic acid to provide a solid 2,5-furandicarboxylic acid.

10. The method in accordance with claim 1, wherein said method is at least partially carried out in a continuous or semi-continuous manner, at least partially in one or more continuous mixed-suspension mixed product removal (MSMPR) crystallizers in series.

11. The method in accordance with claim 5, wherein said method is at least partially carried out in a continuous or semi-continuous manner, at least partially in one or more continuous mixed-suspension mixed product removal (MSMPR) crystallizers in series and wherein said crystallization of the 2,5-furandicarboxylic acid mono salt is carried out in one or more first continuous MSMPR crystallizer and said crystallization of 2,5-furandicarboxylic acid is carried out in one or more second continuous MSMPR crystallizer that is connected to the first MSMPR crystallizer, with optionally a filtration device located between said first and second MSMPR crystallizers.

12. Monosodium 2,5-furandicarboxylic acid, obtainable in accordance with claim 1.

13. The monosodium 2,5-furandicarboxylic acid in accordance with claim 12, wherein monosodium 2,5-furandicarboxylic acid is a monohydrate.

14. Use of a 2,5-furandicarboxylic acid mono salt for the purification of 2,5-furandicarboxylic acid or a salt thereof and/or for providing solid 2,5-furandicarboxylic acid.

15. The method in accordance with claim 2, wherein the 2,5-furandicarboxylic acid mono salt comprises a cation selected from the group consisting of sodium, potassium, lithium, magnesium, calcium, ammonium ($NH_4^+$), tetraalkyl ammonium, and combinations thereof.

16. The method in accordance with claim 2, wherein the 2,5-furandicarboxylic acid mono salt comprises a sodium cation.

17. The method in accordance with claim 4, wherein crystallizing the 2,5-furandicarboxylic acid mono salt is carried out by adjusting the pH of the first aqueous fluid to a pH in the range of 2 to 6.

18. The method in accordance with claim 4, wherein crystallizing the 2,5-furandicarboxylic acid mono salt is carried out by adjusting the pH of the first aqueous fluid to a pH of about 3.

19. The method of claim 6, wherein crystallizing the 2,5-furandicarboxylic diacid is carried out by adjusting the pH of the second aqueous fluid to a pH in the range of 0 to 1.7.

20. The method in accordance with claim 7, wherein the method further comprises filtration of the crystallized 2,5-furandicarboxylic acid mono salt to provide a residue comprising the 2,5-furandicarboxylic acid mono salt.

* * * * *